U.S. PATENT DOCUMENTS

| | | | |
|---|---|---|---|
| 4,301,093 A | 11/1981 | Eck .................................. 261/1 |
| 4,334,531 A | 6/1982 | Reichl et al. ............ 128/200.14 |
| 4,336,544 A | 6/1982 | Donald et al. ................ 346/1.1 |
| 4,338,576 A | 7/1982 | Takahashi et al. ............ 331/67 |
| 4,368,476 A | 1/1983 | Uehara et al. ........... 346/140 R |
| 4,389,071 A | 6/1983 | Johnson, Jr. et al. .......... 299/14 |
| 4,408,719 A | 10/1983 | Last ............................. 239/102 |
| 4,431,136 A | 2/1984 | Janner et al. ................ 239/102 |
| 4,454,877 A | 6/1984 | Miller et al. ............ 128/200.21 |
| 4,465,234 A | 8/1984 | Maehara et al. ............. 239/102 |
| 4,474,251 A | 10/1984 | Johnson, Jr. ..................... 175/67 |
| 4,474,326 A | 10/1984 | Takahashi ................... 239/102 |
| 4,475,113 A | 10/1984 | Lee et al. ..................... 346/1.1 |
| 4,479,609 A | 10/1984 | Maeda et al. ............... 239/102 |
| 4,530,464 A | 7/1985 | Yamamoto et al. ......... 239/102 |
| 4,533,082 A | 8/1985 | Maehara et al. ............. 239/102 |
| 4,539,575 A | 9/1985 | Nilsson ................. 346/140 R |
| 4,544,933 A | 10/1985 | Heinzl .................... 346/140 R |
| 4,546,361 A | 10/1985 | Brescia et al. .......... 346/140 R |
| 4,550,325 A | 10/1985 | Viola ..................... 346/140 R |
| 4,591,883 A | 5/1986 | Isayama ................. 346/140 R |
| 4,593,291 A | 6/1986 | Howkins .................... 346/1.1 |
| 4,605,167 A | 8/1986 | Maehara ..................... 239/102 |
| 4,620,201 A | 10/1986 | Heinzl et al. ........... 346/140 R |
| 4,628,890 A | 12/1986 | Freeman ..................... 123/593 |
| 4,632,311 A | 12/1986 | Nakane et al. ............... 239/101 |
| 4,659,014 A | 4/1987 | Soth et al. ................ 239/102.2 |
| 4,681,264 A | 7/1987 | Johnson, Jr. ............. 239/589.1 |
| 4,693,853 A * | 9/1987 | Falb et al. .................. 261/39.1 |
| 4,702,418 A | 10/1987 | Carter et al. ................ 239/101 |
| 4,722,906 A | 2/1988 | Guire ............................ 436/501 |
| 4,753,579 A | 6/1988 | Murphy ....................... 417/322 |
| 4,790,479 A | 12/1988 | Matsumoto et al. ..... 239/102.2 |
| 4,793,339 A | 12/1988 | Matsumoto et al. ... 128/200.16 |
| 4,796,807 A | 1/1989 | Bendig et al. ........... 239/102.2 |
| 4,799,622 A | 1/1989 | Ishikawa et al. ......... 239/102.2 |
| 4,826,759 A | 5/1989 | Guire et al. ..................... 435/4 |
| 4,828,886 A | 5/1989 | Hieber ....................... 427/422 |
| 4,850,534 A | 7/1989 | Takahashi et al. ........ 239/102.2 |
| 4,865,006 A | 9/1989 | Nogi et al. ................... 123/590 |
| 4,877,989 A | 10/1989 | Drews et al. ................ 310/323 |
| 4,888,516 A | 12/1989 | Daeges et al. ............... 310/323 |
| 4,934,358 A * | 6/1990 | Nilsson et al. ......... 128/200.23 |
| 4,964,521 A | 10/1990 | Wieland et al. |
| D312,209 S | 11/1990 | Morrow et al. ............... D9/371 |
| 4,968,299 A | 11/1990 | Ahlstrand et al. ............. 604/90 |
| 4,973,493 A | 11/1990 | Guire ............................. 427/2 |
| 4,976,259 A | 12/1990 | Higson et al. ......... 128/200.18 |
| 4,979,959 A | 12/1990 | Guire ........................... 623/66 |
| 4,994,043 A | 2/1991 | Ysebaert ..................... 604/191 |
| 5,002,582 A | 3/1991 | Guire et al. .................. 623/66 |
| 5,021,701 A | 6/1991 | Takahashi et al. ........... 310/345 |
| 5,063,396 A | 11/1991 | Shiokawa et al. ....... 346/140 R |
| 5,063,922 A | 11/1991 | Hakkinen ............... 128/200.16 |
| 5,073,484 A | 12/1991 | Swanson et al. ........... 435/7.92 |
| 5,076,266 A | 12/1991 | Babaev .................. 128/200.16 |
| 5,080,649 A | 1/1992 | Vetter ........................... 604/91 |
| 5,115,803 A | 5/1992 | Sioutas .................. 128/200.23 |
| D327,008 S | 6/1992 | Friedman .................... D9/521 |
| 5,122,116 A * | 6/1992 | Kriesel et al. ................ 604/89 |
| 5,139,016 A | 8/1992 | Waser ................... 128/200.16 |
| 5,152,456 A | 10/1992 | Ross et al. ................ 239/102.2 |
| 5,164,740 A | 11/1992 | Ivri ............................. 346/1.1 |
| 5,170,782 A | 12/1992 | Kocinski ............... 128/200.16 |
| 5,180,482 A | 1/1993 | Abys et al. ................... 205/224 |
| 5,186,164 A | 2/1993 | Raghuprasad ......... 128/200.14 |
| 5,186,166 A | 2/1993 | Riggs et al. ............ 128/203.15 |
| 5,198,157 A | 3/1993 | Bechet ........................... 264/9 |
| 5,213,860 A | 5/1993 | Laing |
| 5,217,492 A | 6/1993 | Guire et al. .................. 623/11 |
| 5,258,041 A | 11/1993 | Guire et al. ................... 623/66 |
| 5,261,601 A | 11/1993 | Ross et al. ................ 239/102.2 |
| 5,263,992 A | 11/1993 | Guire ........................... 623/66 |
| 5,297,734 A | 3/1994 | Toda ....................... 239/102.2 |
| 5,299,739 A | 4/1994 | Takahashi et al. ........ 239/102.2 |
| 5,312,281 A | 5/1994 | Takahashi et al. ............ 446/25 |
| 5,320,603 A | 6/1994 | Vetter et al. ................... 604/82 |
| 5,342,011 A | 8/1994 | Short ........................... 248/318 |
| 5,347,998 A | 9/1994 | Hodson et al. ......... 128/200.23 |
| 5,414,075 A | 5/1995 | Swan et al. ................. 568/333 |
| 5,415,161 A | 5/1995 | Ryder .................... 128/200.23 |
| 5,431,155 A | 7/1995 | Marelli .................. 128/200.14 |
| 5,435,282 A | 7/1995 | Haber et al. ........... 128/200.16 |
| D362,390 S | 9/1995 | Weiler ......................... D9/520 |
| 5,452,711 A | 9/1995 | Gault ..................... 128/200.14 |
| 5,458,135 A | 10/1995 | Patton et al. ........... 128/200.14 |
| 5,477,992 A | 12/1995 | Jinks et al. ............... 222/402.2 |
| 5,487,378 A | 1/1996 | Robertson et al. ..... 128/200.16 |
| 5,489,266 A | 2/1996 | Grimard ........................ 604/82 |
| D369,212 S | 4/1996 | Snell .......................... D24/117 |
| 5,512,329 A | 4/1996 | Guire et al. ................. 427/508 |
| 5,512,474 A | 4/1996 | Clapper et al. ........ 438/240.243 |
| 5,515,841 A | 5/1996 | Robertson et al. ..... 128/200.15 |
| 5,515,842 A | 5/1996 | Ramseyer et al. ..... 128/200.18 |
| 5,518,179 A | 5/1996 | Humberstone et al. .. 239/102.2 |
| 5,529,055 A | 6/1996 | Gueyet .................. 128/200.16 |
| 5,533,497 A | 7/1996 | Ryder .................... 128/200.21 |
| 5,563,056 A | 10/1996 | Swan et al. ................. 435/180 |
| D375,352 S | 11/1996 | Bologna .................... D24/115 |
| 5,579,757 A | 12/1996 | McMahon et al. ..... 128/200.21 |
| 5,586,550 A | 12/1996 | Ivri et al. ............... 128/200.16 |
| 5,601,077 A | 2/1997 | Imbert .................... 128/200.14 |
| 5,637,460 A | 6/1997 | Swan et al. ..................... 435/6 |
| 5,647,349 A * | 7/1997 | Ohki et al. ............. 128/203.15 |
| 5,654,007 A | 8/1997 | Johnson et al. ............. 424/489 |
| 5,654,162 A | 8/1997 | Guire et al. ................ 435/7.92 |
| 5,654,460 A | 8/1997 | Rong ........................... 556/472 |
| 5,665,068 A | 9/1997 | Takamura .................... 604/90 |
| 5,692,644 A | 12/1997 | Gueret ......................... 222/80 |
| 5,707,818 A | 1/1998 | Chudzik et al. ............ 435/7.93 |
| 5,714,360 A | 2/1998 | Swan et al. ................. 435/174 |
| 5,714,551 A | 2/1998 | Bezwada et al. ........... 525/411 |
| D392,184 S | 3/1998 | Weiler ......................... D9/302 |
| 5,744,515 A | 4/1998 | Clapper ...................... 523/113 |
| 5,758,637 A | 6/1998 | Ivri et al. ............... 128/200.16 |
| 5,810,004 A * | 9/1998 | Ohki et al. ............. 128/203.15 |
| 5,819,730 A | 10/1998 | Stone et al. |
| 5,878,900 A | 3/1999 | Hansen |
| 5,897,008 A | 4/1999 | Hansen |
| 5,938,117 A | 8/1999 | Ivri ................................ 239/4 |
| 5,954,268 A | 9/1999 | Joshi et al. .................... 239/34 |
| 5,964,417 A * | 10/1999 | Amann et al. ............... 239/338 |
| 6,007,518 A | 12/1999 | Kriesel et al. .............. 604/131 |
| 6,014,970 A | 1/2000 | Ivri et al. ............... 128/200.14 |
| 6,045,874 A | 4/2000 | Himes ......................... 427/424 |
| 6,062,212 A | 5/2000 | Davison et al. |
| 6,068,148 A | 5/2000 | Weiler |
| 6,085,740 A | 7/2000 | Ivri et al. ............... 128/200.16 |
| 6,096,011 A | 8/2000 | Trombley, III et al. ..... 604/256 |
| 6,106,504 A | 8/2000 | Urrutia ........................ 604/251 |
| 6,186,141 B1 * | 2/2001 | Pike et al. ............. 128/203.12 |
| 6,205,999 B1 | 3/2001 | Ivri et al. |
| 6,235,177 B1 | 5/2001 | Borland et al. |

FOREIGN PATENT DOCUMENTS

| | | |
|---|---|---|
| EP | 0 476 991 B1 | 3/1995 |
| FR | 2 692 569 A1 | 6/1992 |
| GB | 973458 | 10/1964 |
| GB | 1454597 | 11/1976 |
| GB | 2 073 616 A | 10/1981 |
| GB | 2 101 500 | 1/1983 |

| | | | | |
|---|---|---|---|---|
| GB | 2 177 623 A | | 1/1987 | |
| GB | 2 240 494 A | | 8/1991 | |
| GB | 2 272 389 A | | 5/1994 | |
| GB | 2 279 571 A | | 1/1995 | |
| JP | 57-23852 | | 2/1982 | |
| JP | 57-105608 | | 7/1982 | |
| JP | 58-61857 | | 4/1983 | |
| JP | 58-139757 | | 8/1983 | |
| JP | 60-4714 A | | 1/1985 | |
| JP | 61-8357 A | | 1/1986 | |
| JP | 61-215059 A | | 9/1986 | |
| JP | 2-135169 | | 5/1990 | |
| JP | 2-189161 | | 7/1990 | |
| WO | WO 92/07600 | | 5/1992 | |
| WO | WO 92/11050 | | 7/1992 | |
| WO | WO92/17231 | * | 10/1992 | ............ 128/200.23 |
| WO | WO 93/01404 | | 1/1993 | |
| WO | WO 96/09229 | | 3/1996 | |
| WO | WO 99/63746 | | 12/1999 | |

OTHER PUBLICATIONS

Ueha, S., et al. Mechanism of Ultrasonic Atomization Using a Multi–Pinhole Plate. J. Acoust. Soc. Jpn. (E) 6,1:21 (1985).

Maehara, N., et al. Influence of the Vibrating System of a Multipinhole–plate Ultrasoic Nebulizer on Its Performance. Review of Scientific Instruments, 57 (11), Nov. 1986, pp. 2870–2876.

Maehara, N., et al. Optimum Design Procedure for Multi–Pinhole–plate Ultrasonic Atomizer. Japanese Journal of Applied Physics, 26:215 (1987).

Ashgriz, N., et al. Development of a Controlled Spray Generator. Rev. Sci. Instrum. 58(7):1291 (1987).

Hikayama, H., et al. Ultrasonic Atomizer with Pump Function. Tech. Rpt. IEICE Japan US88–74:25 (1988).

J. Acousticl Soc. Japan 44:2:116 (1988).

J. Acoustical Soc. Japan 44:6:425 (1988).

Siemens AG, 1989,"Ink–Jet Printing: The Present State of the Art," by Wolfgang R. Wehl.

TSI Incorporated product catalog. Vibrating Orifice Aerosol Generator (1989).

Gaiser Tool Company catalog, pp. 26, 29–30 (19__).

Nogi, T., et al. Mixture Formation of Fuel Injection System in Gasoline Engine. Nippon Kikai Gakkai Zenkoku Taikai koenkai Ronbunshu 69:660 (1991).

D.C. Cipolla et al., "Assessment of Aerosol Delivery systems for Recomvinant Human Deoxyribonuclease," *S.T.P. Pharma Sciences* 4 (1) 50–62, 1994.

D.C. Cipolla et al., "Characterization of Aerosols of Human Recombinant Deoxyribonuclease I (rhDNase) Generated by Jet Nebulizers," *Pharmaceutical Research* II (4) 491–498, 1994.

I. Gonda, "Therapeutic Aerosols," *Pharmaceuticals, The Sci. of Dosage Form Design,* M.E. Aulton, 341–358, 1988.

Anthony J. Hickey, "Pharmaceutical Inhalation Aerosol Technology," *Drugs And The Pharmaceutical Sciences,* (54) 172–173.

J.A. Abys et al., "Annealing Behavior of Palladium–Nickel All Electrodeposits," pp. 1–7.

"Palla Tech Pd an Pd Alloy Processes—Procedure for the Analysis of Additive IVS in Palla Tech Plating Solutions by HPLC," *Technical Bulletin,* Electroplating Chemicals & Services, 029–A, Lucent Technologies, , pp. 1–5, 1996.

M.C. Manning et al., "Stability of Protein Pharmaceuticals," *Pharmaceutical Research* 6, 903–918 (1989).

B.C. Hancock et al., "Molecular Mobility of Amorphous Pharmaceutical Solids Below Their Glass Transition Temperatures," *Pharmaceutical Research* 12, 799–806 (1995).

* cited by examiner

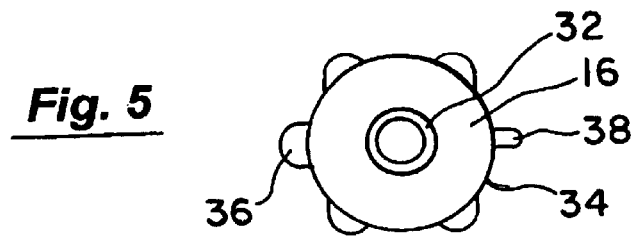
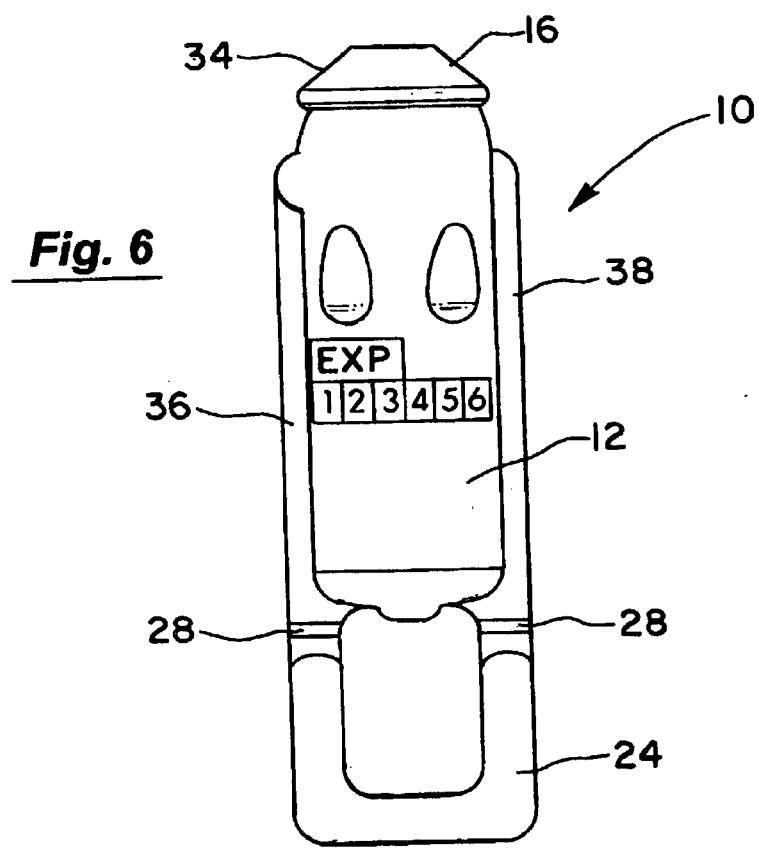
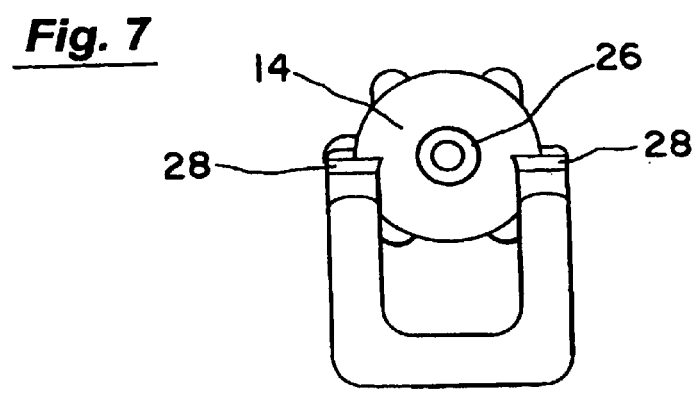

FLUID FILLED AMPOULES AND METHODS FOR THEIR USE IN AEROSOLIZERS

BACKGROUND OF THE INVENTION

This invention relates generally to the field of liquid aerosolization, and in particular to the management of liquids used in the aerosolization process. More specifically, the invention relates to ampoules containing liquids that are to be aerosolized.

The ability to aerosolize or nebulize small liquid droplets is important to a variety of industries. Merely by way of example, many pharmaceuticals can now be delivered to the lungs in liquid form. Aerosolization is also a useful technique to dispense deodorizers, perfumes, insecticides or the like into the atmosphere.

Aerosolizers or nebulizers typically utilize a supply of liquid that is contained in some type of reservoir, such as a container, canister, or the like. In this way, the liquid may be stored in a sealed environment until ready for aerosolization, However, because the liquid is sealed within a container, the fluid needs to be removed and transferred to the aerosol generator prior to aerosolization. Hence, this invention relates to the use of various ampoules that are employed to store liquids prior to aerosolization, as well as to techniques for accessing and transferring the liquid to an aerosol generator.

BRIEF SUMMARY OF THE INVENTION

In one embodiment, a fluid filled ampoule is provided that comprises an ampoule body having a top end, a bottom end, and a sealed interior containing a liquid. The ampoule body may be manufactured by blowing or vacuum forming the ampoule body in a mold. The ampoule body may then be filed with liquid, and a melt sealing process may be used to seal the liquid within the ampoule body. The ampoule further includes a top tab that is coupled to the top end and a bottom tab that is coupled to the bottom end. In this way, the top tab may be removed to create a drain vent in the top end while the bottom tab may be removed to create a drain opening in the bottom end. Conveniently, the top and bottom tabs may be removed by twisting the tabs. Alternatively, the tabs may be crack tabs where material is not completely removed but the seal is broken. Combinations of twist and crack tabs may also be used. Further, in one alternative, the ampoule may be constructed to be pierced at either the top end and/or the bottom end to create the vent or drain opening.

In one aspect, the ampoule may include a shroud that is coupled to the top end so that it is disposed about the top tab. In this way, the top tab is prevented from being removed until first moving or bending the shroud away from the top tab. Such a shroud is useful in ensuring the proper order of removal of the top and bottom tabs. For example, by preventing access to the top tab, a user may be trained to first remove the bottom tab. Once removed, the ampoule may then be placed into an aerosolization device. In so doing, the liquid remains within the ampoule because no vent has yet been provided. When the ampoule is within the aerosolization device, the shroud may be bent and the top tab removed to create the vent opening. Upon creation of the vent opening, the liquid flows into the aerosolization device where it is available for aerosolization.

In another aspect, the ampoule may include one or more orientation elements to ensure proper orientation of the ampoule when it is inserted into an aerosolization device. For example, the ampoule body may include a pair of longitudinal rails that are adapted to guide the ampoule into a receiver of an aerosolization device. Conveniently, the rails may have different sizes so that the ampoule may be inserted into the receiver in only one orientation.

In a further aspect, the ampoule may include one or more keying elements that are used to ensure that the correct ampoule is used in an aerosolization device. The keying elements may be used to prevent insertion of the ampoule into an aerosolization device if the ampoule is not the correct ampoule. Such keying elements may include, for example, one or more protrusions that extend from the ampoule body. These protrusions must fit within corresponding slots within the aerosolization device to permit the ampoule to be inserted. Alternatively, the keying element may be configured to prevent operation of the aerosolization device unless recognized by the aerosolization device. For example, the ampoule body may include a readable pattern, such as a bar code, a magnetic pattern, or the like, which must be recognized by the aerosolization device before operation will be permitted. In another aspect, the ampoule may include one or more protrusions to trigger an electrical switch which closes a circuit in the aerosol generator. Such a trigger may be used to supply power to the aerosol generator. When the user inhales, a flow sensor may be actuated to fully power up the aerosol generator to aerosolize the liquid. If the correct protrusions are not included on the ampoule, the aerosol generator will not actuate.

In a further aspect, the ampoule may be provided with a large sealing surface that is configured to provide a seal with the aerosol generator. The large sealing surface is advantageous in that it leaves a relatively large, empty socket in the aerosolization device after the ampoule is removed. In this way, the aerosolization device may more easily be accessed during cleaning after the ampoule has been removed. The large sealing surface may conveniently be provided by tapering the bottom end to increase the surface area. In yet another aspect, the ampoule is provided with a relatively thick wall to reduce the chance of droplet spillage. For example, the ampoule body may be provided with a wall thickness of at least about 0.03 inches.

BRIEF DESCRIPTION OF THE DRAWINGS

FIG. 5 is a bottom-end view of the ampoule of FIG. 1 after the removal of a bottom tab to expose a drain opening.

FIG. 6 is a side view of the ampoule of FIG. 5 and further illustrating the removal of a top tab to expose a vent opening.

FIG. 7 is a top view of the ampoule of FIG. 6 and further illustrating the bending of a shroud to gain access to the top tab (shown removed).

DESCRIPTION OF THE SPECIFIC EMBODIMENTS

Figure 1:
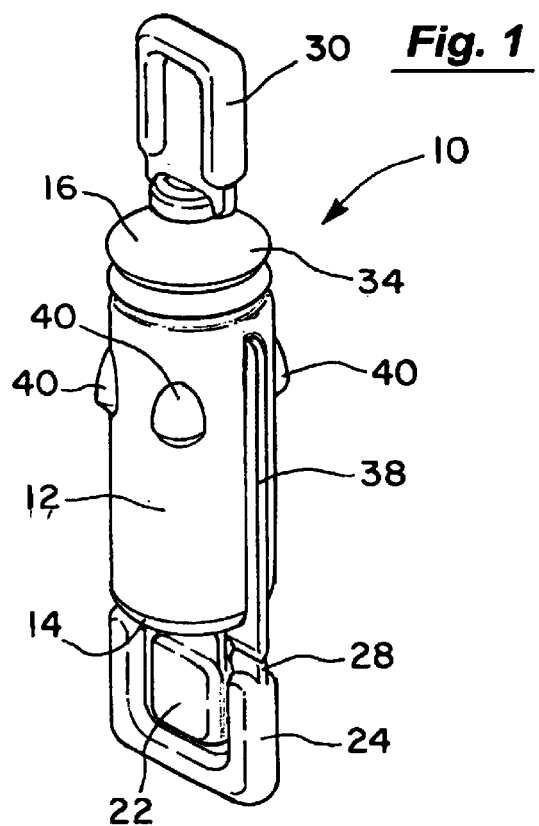
FIG. 1 is a perspective view of one embodiment of an ampoule according to the invention.

The invention provides various ampoules used to store liquids that are to be atomized as well as techniques for transferring the stored liquids to an aerosolizer. The ampoules of the invention may conveniently include a variety of features to facilitate their use within various types of aerosolization devices. Such features may include, for example, features to insure their proper insertion into an aerosolization device, to insure proper operation of the ampoules when releasing the stored liquids, and to insure that the correct ampoule is being inserted into the aerosolization device.

The ampoules of the invention may be used with a wide variety of aerosolization devices that are configured to aerosolize a volume of liquid. Such aerosolizers may be of the type, for example, where a vibratable member is vibrated at ultrasonic frequencies to produce liquid droplets. Some specific, non-limiting examples of technology for producing fine liquid droplets is by supplying liquid to an aperture plate having a plurality of tapered apertures and vibrating the aperture plate to eject liquid droplets through the apertures. Such a technique is described generally in U.S. Pat. Nos. 5,164,740; 5,938,117; 5,586,550; 5,758,637 and 6,085,740, the complete disclosures of which are herein incorporated by reference. However, it will be appreciated that the invention is not intended to be limited for use only with such devices.

The ampoules of the invention may be used to store a wide variety of liquids. Merely by way of example, liquids that may be stored within the ampoules include various pharmaceuticals such as saline, albuterol, chromatin, budesinide, nicotine, THC, cocaine, and the like. Other liquids that may be stored include insecticides, deodorizers, perfumes, and the like. Hence, it will be appreciated that the ampoules of the invention may be used to store essentially any type of liquid that is capable of being aerosolized.

The ampoules of the invention may be constructed by blowing or vacuum-forming the ampoule in a mold, filling the ampoule with liquid, and melt-sealing the liquid into the ampoule. The ampoules may further be provided with a set of removable tabs to provide a drain vent and a drain opening. Typically, these will be located in the top and bottom of the ampoule so that the liquid may drain by force of gravity once the openings are formed. The tabs may be removed by twisting, cracking, or the like so that the opening may be formed. In some cases, the ampoules may be configured to be opened simply by piercing the top and/or bottom end. Such piercing elements may conveniently be incorporated into the aerosolization device.

Various materials may be used to construct the ampoules, such as moderate durometer polymer materials, thermoplastic synthetics, such as low density polyethylene and polypropylene, and the like. The ampoules may be provided with a thick enough wall to minimize droplet spillage. For instance, the wall thickness may be greater than about 0.030 inch. The ampoule may further be configured so that the diameter of the drain opening minimizes the drip potential for the fluid stored within the ampoule. For example, larger diameter openings may be provided when storing higher viscosity fluids and smaller diameter openings may be used for low viscosity fluids.

The ampoules may include one or more orienting elements to ensure proper orientation of the ampoule when inserted into an aerosolization device. For example, the ampoule may include one or more keyed rails that must be inserted into the appropriate slots in the aerosolization device. One way to key the rails is by making them of different widths so that each rail must be inserted into a specific slot in the aerosolization device. Conveniently, the difference in width may be accomplished by thickening the entire length, or by the incorporation of one or more discrete points of thicknesses, which may be either at the top, bottom or any combination of points along the length of the rail. The use of discrete width increases in the rails is advantageous in that it decreases the addition of voids in the fill space and thus reduces the hold-up volume of the ampoule when drained.

Another feature of the ampoules is that they may include in their physical design an order of operation. In other words, the ampoule may be configured so that it is operated in a certain way when removing the liquid. For example, the first twist-off tab to be used may be unrestricted and easily accessible to the user. On the other hand, access to the second twist-off tab may be prevented access until a prior operation, such as the folding of a shroud, is performed in order to expose the second twist-off tab.

The use of a folding shroud may also be used as a handle for removal of the ampoule after drainage of the fluid. Such a handle may also be used to place the ampoule into the space in which it is loaded in the aerosolization device.

Another feature of the ampoules is that they may be provided with a large sealing surface as well as a large ratio of the sealing surface to the twist-off tab for the drain opening. The sealing surface may be provided with a large diameter so that the empty socket which remains after the ampoule is removed may easily be cleaned. The seal between the ampoule and the aerosolization device may be made between the outside diameter of the ampoule and the inside diameter of a receiver in the aerosolization device. However, this seal may also made between the inside of the ampoule and the outside of the aerosolization device receiver.

In another embodiment, the ampoule may be constructed so that it may not be used with some aerosolization devices, or so that it may fit within more than one device. For example, the ampoule may include male or female protrusions that may be used to key the ampoule to a specific aerosolization device or devices. The presence of such a keying feature on the aerosolization device receiver would require the same key feature to be on the ampoule. However, some ampoules with the same pattern, but a different number of keying protrusions or intrusions may be accepted by multiple front ends of aerosolization devices. An ampoule may be configured to be excluded or included into a specific aerosolization device by choosing the number and/or location of the keying protrusions or inclusions.

The ampoules may alternatively be provided with a variety of other keying features, such as by using a thin metallic strip that is attached to the side or face of the ampoule. For example, the strip may be bonded to the ampoule, molded into the ampoule, or crimped onto the side of the ampoule after production. The strip may have a series of alternating metallic areas where a reader in the aerosolization device may read the pattern on the surface through a resistance method to identify the type of drug in the ampoule, the expiration date, the dosage to be delivered, or any other information that may accompany the ampoule. As another alternative, the ampoule may be bar coded with visible, ultraviolet, or infrared ink to provide the same keying features through a detector mounted within the aerosolization device. Such aerosolization devices may utilize a memory device, a magnetic strip, or other communication device to communicate the specifics of the ampoule to the aerosolization device. The controller of the aerosolization device may also be configured to provide feedback, to keep a tally of the total doses taken, or other information.

A further alternative for keying the ampoule may be to provide protrusions molded into the side of the ampoule on the keying rail. These protrusions or nubs may either stick out in line with the plane made by the two side rails or may be mounted 90 degrees relative to this plane. The side rails may be of different widths, and of different overall lengths, as well as shapes that are different from each other or that are different from other ampoules. The rail may have a variety of shapes, such as square, rounded, triangular, angled, or the like, and may also be applied to the overall volume of the ampoule for a unique keying strategy.

Such protrusions may be used to close an electromechanical circuit when inserted into the aerosolization device. Once the circuit is closed, power is provided to the aerosol generator. For example, the aerosol generator may be placed in sleep or silent mode. When the user inhales, a flow sensor senses the breath and increases the power to the aerosol generator to aerosolize the liquid.

Referring now to FIGS. 1–4, one embodiment of an ampoule 10 will be described. Ampoule 10 comprises an ampoule body 12 having a top end 14 and a bottom end 16. Ampoule body 12 has a sealed interior 18 containing a liquid 20 (see FIGS. 4A and 4B). Ampoule body 12 may be constructed by blowing or vacuum-forming the ampoule body in a mold. The ampoule body may then be filled with liquid 20 and a melt-sealing process used to seal the fluid within ampoule body 10.

Integrally formed with ampoule body 12 at top end 14 is a top tab 22 that is surrounded by a bendable shroud 24. Tab 22 is removable from ampoule body 12 by grasping tab 22 and twisting it relative to ampoule body 12. Once tab 22 is removed, a drain vent 26 is formed in top end 14 as best shown in FIG. 7. To permit tab 22 to be twisted off, shroud 24 is bent relative to ampoule body 12 as illustrated generally in FIG. 7. Conveniently, recesses 28 may be provided in shroud 24 to facilitate bending of shroud 24 to provide access to tab 22.

Integrally formed with ampoule body 12 at bottom end 16 is a bottom tab 30 to form a drain opening 32 as best shown in FIG. 5. Conveniently, bottom tab 30 may be configured to be twisted off in a manner similar to top tab 22 to form drain opening 32.

When both drain vent 26 and drain opening 32 are formed, liquid 20 is permitted to drain through drain opening 32 by force of gravity (assuming top end 14 is vertically above bottom end 16). In use, ampoule 10 may need to be inserted into an aerosolization device. Conveniently, the aerosolization device may include a receiver into which ampoule 10 is inserted. Merely by way of example, ampoule 10 may be inserted into a receiver as described in co-pending U.S. application Ser. No. 09/812,987, filed on the same date as the present application, the complete disclosure of which is herein incorporated by reference. Ampoule 10 is configured to ensure the proper order of tab removal when using ampoule 10 with an aerosolization device. For example, shroud 24 prevents access to top tab 22, thereby suggesting to the user that tab 30 should first be removed in order to create the drain opening. Once tab 30 is removed, ampoule 10 may be inserted into an aerosolization device, with liquid being prevented from exiting through drain opening 32 by the vacuum existing within interior 18. Once within the device, shroud 24 may be bent to the side and top tab 22 twisted off to provide drain vents 26. In so doing, liquid 20 is free to flow from ampoule body 12 and into the aerosolization device where it may be aerosolized.

Bottom end 16 includes an outer edge 34 that is used to form a seal between ampoule body 12 and the aerosolization device into which ampoule 10 is inserted. Outer edge 34 has a relatively large diameter so that the socket into which ampoule 10 is inserted is also relatively large. In this way, the empty socket in the aerosolization device may easily be cleaned following removal of ampoule 10. Merely by way of example, outer edge 34 may have a diameter in the range from about 0.2 inch to about 1 inch.

Figure 4:
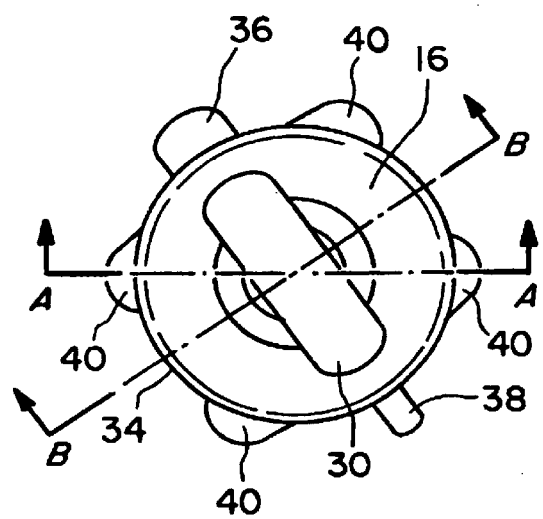
FIG. 4 is a bottom-end view of the ampoule of FIG. 1.
Figure 4A:
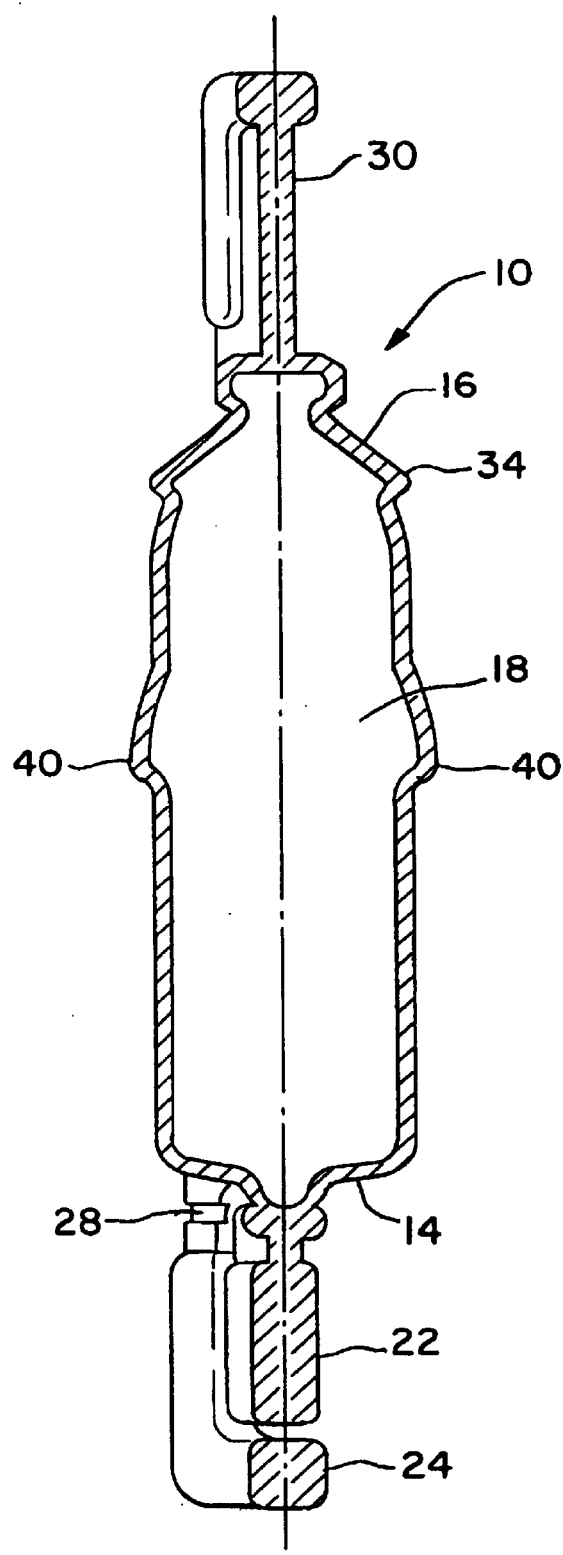
FIG. 4A is a cross-sectional side view of the ampoule of FIG. 4 taken along lines A—A.
Figure 4B:
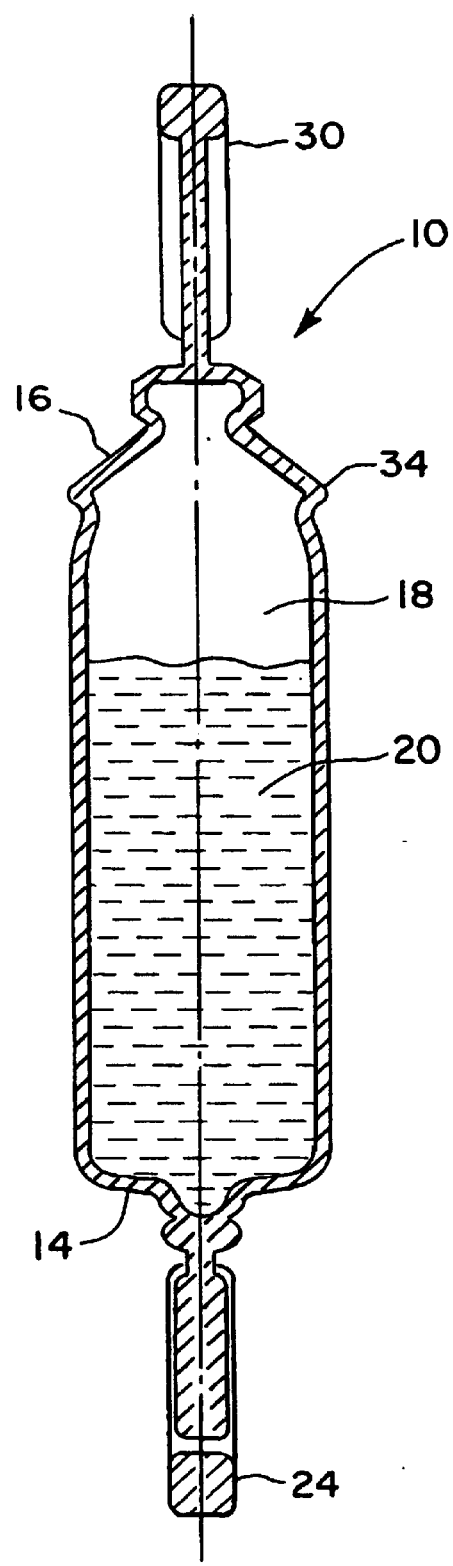
FIG. 4B is a cross-sectional side view of the ampoule of FIG. 4 taken along lines B—B.

Ampoule body 12 includes a pair of longitudinal rails 36 and 38. As best shown in FIG. 4, rail 36 is thicker than rail 38. In this way, rails 36 and 38 are keyed to ensure proper orientation of ampoule 10 into an aerosolization device. For example, the aerosolization device may include a receiver having a wide slot and a narrow slot that are configured to receiver rails 36 and 38, respectively.

Ampoule further includes a set of keying protrusions 40 that protrude from ampoule body 12. Protrusions 40 are used to key ampoule 10 so that it may be inserted only into aerosolization devices that are specifically configured to receive such an ampoule. For example, as shown, ampoule 10 includes four protrusions 40. With such a configuration, the aerosolization device may include four slots that are configured to receive protrusions 40. The slots have the same dimension and are at the same angle of orientation so that ampoule 10 may be inserted into the aerosolization device. To vary the keying features, ampoule 10 may be provided with a different number of protrusions, or by changing the size and/or position of protrusions 40 on ampoule body 12. In this way, ampoule 10 may be keyed for a specific device. With such a configuration, a drug may be placed into ampoule 10 which is specifically configured for a certain aerosolization device. If the ampoule containing the proper drug is not inserted into the aerosolization device, the drug may not be aerosolized. Although shown with protrusions, it will be appreciated that a wide variety of other keys may be used to key ampoule 10 as previously described. Further, other specific examples of keying features will be described hereinafter with reference to FIGS. 9 and 10.

Figure 2:
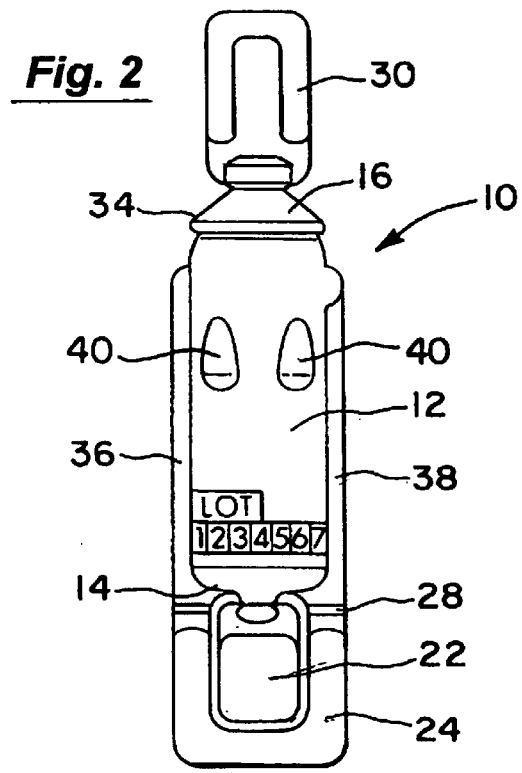
FIG. 2 is a front view of the ampoule of FIG. 1.
Figure 3:
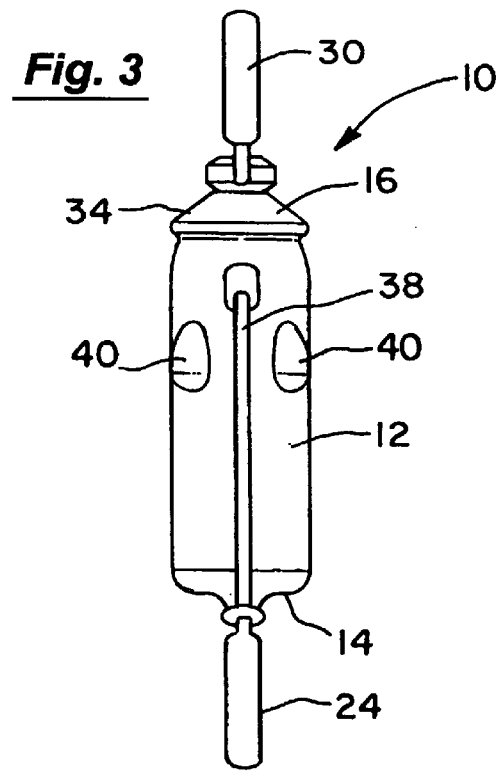
FIG. 3 is a side view of the ampoule of FIG. 1.

As shown in FIGS. 2 and 6, various information may be molded into ampoule body 12. For example, the lot number of the ampoule and the expiration date of the drug may be molded into ampoule body 12. Further, it will be appreciated that other descriptive information may also be included on ampoule body 12.

Figure 8:
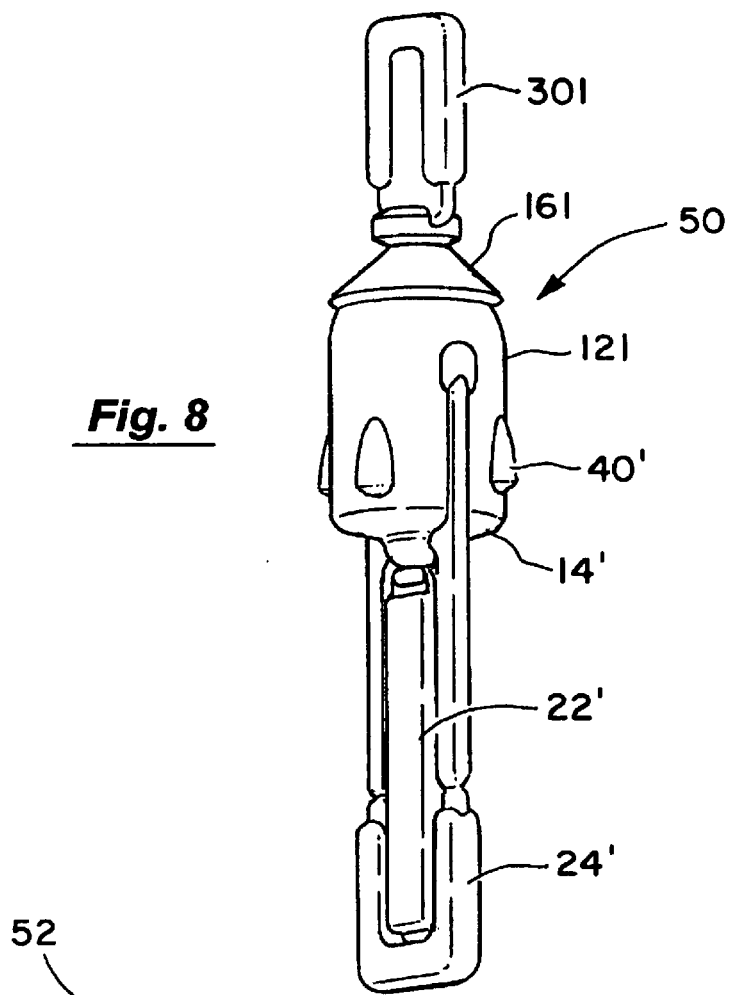
FIG. 8 is a perspective view of an alternative ampoule according to the invention.

Shown in FIG. 8 is an alternative embodiment of an ampoule 50. Ampoule 50 is essentially identical to ampoule 10 except for the size of various components. For convenience of illustration, similar components will be referred to using the same reference numerals followed by a prime ("'"). Ampoule body 12' of ampoule 50 is significantly smaller than ampoule body 12. In this way, ampoule 50 may be used for drugs requiring less of a unit dosage. Because ampoule body 12' has been reduced in size, top tab 22' and shroud 24' are made larger so that ampoule 50 retains the same overall size as ampoule 12. In this way, a variety of ampoules that contain different unit dosages may be used within the same type of aerosolization devices. Merely by way of example, ampoule 50 may be configured to hold a volume of about 0.2 mL to about 1.0 mL while ampoule 10 may hold a volume of about 0.2 mL to about 6 mL, and more preferably from about 0.8 mL to about 3.0 mL. For other aerosolization applications, such as when aerosolizing a deodorizer or insecticizer, larger volumes may be used.

Figure 9:
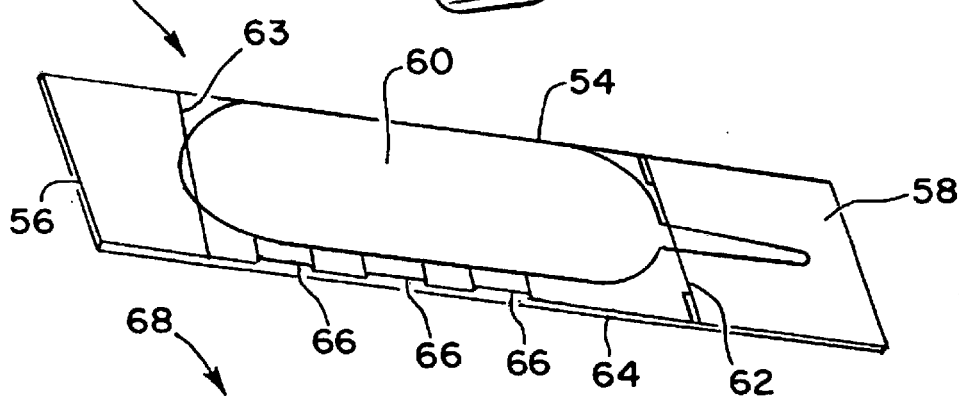
FIG. 9 is a perspective view of an ampoule having contact points that serve as keying element according to the invention.

FIG. 9 illustrates an alternative embodiment of an ampoule 52. Ampoule comprises an ampoule body 54 having a top end 56 and a bottom end 58. Ampoule body 54 includes a reservoir 60 that contains a liquid. Ampoule body 54 includes score lines 62 that permit bottom end 58 to be broken off from ampoule body 54 to provide a drain opening, and score lines 63 to permit top end 56 to be broken off to provide a vent. Conveniently, a piercing mechanism may be used to pierce reservoir 60 to permit the liquid to drain from reservoir 60.

Ampoule body 54 further includes a side 64 that includes a series of alternating metallic areas 66. In this way, when ampoule 52 is inserted into an aerosolization device, an electrical reader may be used to read the pattern of metallic areas 66 to determine the liquid contained within reservoir 66. If the appropriate ampoule has not been inserted, the aerosolization device may include a controller to prevent its operation. Although shown in connection with FIG. 9, it will be appreciated that similar metallic areas may be used within any of the embodiments described herein in order to key the ampoule to a specific type of liquid.

Figure 10:
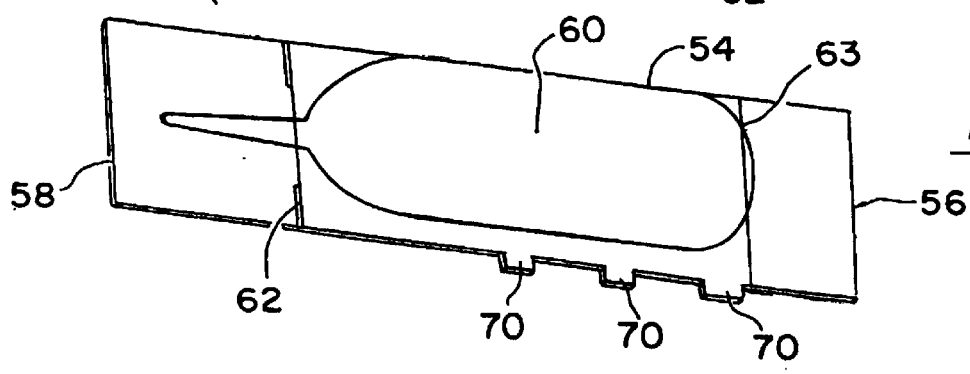
FIG. 10 illustrates another embodiment of an ampoule having contact fingers that are used as keying elements according to the invention.

FIG. 10 illustrates an alternative embodiment of an ampoule 68 that has the same overall appearance to ampoule 52 of FIG. 9. For convenience of discussion, similar elements will be referred to with the same reference numerals. Ampoule 68 differs from ampoule 52 in that it utilizes a set of fingers 70 that serve as keying elements to identify the particular type of liquid contained within reservoir 60. Ampoule 68 may be used within an aerosolization device having spring contact leaves that are actuated to cause a circuit to be created upon insertion. In this way, the aerosolization device recognizes the specific type of ampoule and may be configured to operate only when the proper ampoule has been inserted.

Other techniques for keying such ampoules is by including a metal film on the surface of the ampoule body. This may be accomplished by plating, spraying, taping or any other attachment scheme. The attached metal may be selectively covered by paint or may be attached only in certain areas. The presence of the metal serves as a conductor and patterns of the conductive material may cause the aerosolization device to recognizes the particular type of ampoule. For example, the pattern of conductive areas may be sensed by a linear or other set of spring sensors. Such spring tension sensors may serve to both hold the ampoule in place and to push the contacts against the ampoule body to make a reliable contact. Such a scheme may be used with any of the ampoules described herein.

In some embodiments, the ampoule may be provided with a programmable memory chip, such as an EPROM chip that is on the surface or embedded as part of the manufacturing process. The aerosolization device may include a reader to read the information from the memory. In this way, the aerosolizer may keep a record of various information, such as the number of doses, the time of dosing, the expiration date, and the like.

The invention has now been described in detail for purposes of clarity of understanding. However, it will be appreciated that certain changes and modifications may be practiced within the scope of the appended claims.

What is claimed is:

1. A method for supplying liquid to an aerosolization device, the method comprising:

providing an ampoule comprising an ampoule body having a top end, a bottom end, and a sealed interior containing a liquid, an air vent disposed near the top end, and a bottom tab that is coupled to the bottom end;

removing the bottom tab to create a drain opening;

inserting the ampoule into a receiving portion of the aerosolization device;

opening the air vent;

wherein upon opening of the air vent and the creation of the drain opening, the liquid in the interior flows out of the drain opening and into the aerosolization device where it is available for aerosolization by the aerosolization device.

2. A method as in claim 1, further comprising inserting the ampoule into the aerosolization device after removing the bottom tab and prior to opening the drain vent.

3. A method as in claim 2, wherein the bottom end is tapered, and further comprising providing a seal with the bottom end and the aerosolization device.

4. A method as in claim 1, wherein the ampoule includes a top tab that is removable to form the air vent and a shroud that is disposed about the top tab, and further comprising bending the shroud to move the shroud away from the top tab.

5. A method as in claim 4, further comprising twisting the top tab and the bottom tab to remove them from the ampoule body.

6. A method as in claim 1, wherein the ampoule further includes a pair of longitudinal rails on the ampoule body, and further comprising inserting the ampoule into the aerosolization device such that the rails are received into corresponding slots in the aerosolization device.

7. A method as in claim 6, wherein the rails and the slots have different sizes, and further comprising inserting the ampoule such that the rails and received into the appropriately sized slots.

8. A method as in claim 1, wherein the ampoule further includes at least one keying element on the ampoule body, and further comprising inserting the aerosolization device and permitting operation of the aerosolization device only when the keying element is accepted by the aerosolization device.

9. A method as in claim 8, wherein the keying element comprises a protrusion on the ampoule body, and further comprising inserting the ampoule into the aerosolization device such that the protrusion is received into a keyed slot in the aerosolization device.

10. A method as in claim 1, wherein the liquid comprises a medicament.

* * * * *